Figure 1:
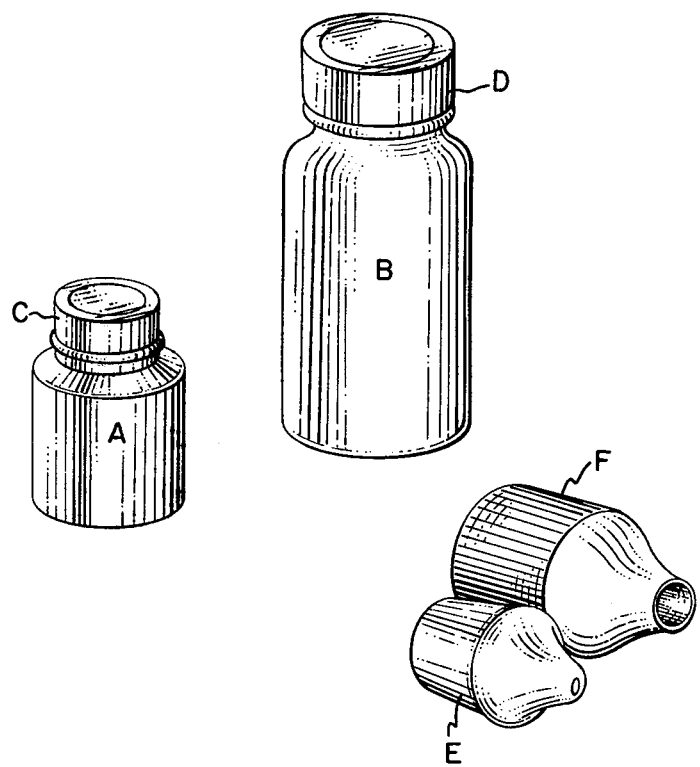

United States Patent [19]

Chrai et al.

[11] 4,255,415
[45] Mar. 10, 1981

[54] POLYVINYL ALCOHOL OPHTHALMIC GEL

[75] Inventors: Sukhbir S. Chrai, Belleville; Santosh Gupta, Bloomfield; Michael J. Hensley, Dover, all of N.J.

[73] Assignee: Schering Corporation, Kenilworth, N.J.

[21] Appl. No.: 962,812

[22] Filed: Nov. 22, 1978

Related U.S. Application Data

[63] Continuation of Ser. No. 816,783, Jul. 18, 1977, abandoned.

[51] Int. Cl.³ .................. A61K 31/74; A61K 31/59; A61K 31/35; A61K 31/415
[52] U.S. Cl. .................. 424/78; 424/148; 424/236; 424/283; 424/273 R; 424/325
[58] Field of Search .............. 424/273, 148, 78, 236, 424/283, 325

[56] References Cited

U.S. PATENT DOCUMENTS

| | | | |
|---|---|---|---|
| 2,703,777 | 3/1955 | Feinstein et al. | 424/148 |
| 2,861,920 | 11/1958 | Dale et al. | 424/78 |
| 3,214,338 | 10/1965 | Ehrlich | 424/78 |
| 3,608,073 | 9/1971 | Phares et al. | 424/273 |
| 3,767,788 | 10/1973 | Rankin | 424/78 |
| 4,003,991 | 1/1977 | Krohn et al. | 424/78 |

FOREIGN PATENT DOCUMENTS 2459391  6/1975  Fed. Rep. of Germany .......... 424/273

OTHER PUBLICATIONS

Invest. Ophthal. Feb. (1975) 14 (2) pp. 87–89, "Ophthalmic Drug Inserts".
Am. J. Ophthalmol. 57 (1) pp. 99–106 (1964)–Krishna et al., PVA as an Ophthalmic Vehicle.
Symposium on Ocular Therapy, 9 pp. 1–16 (1977), Maichuk–"Polymeric Drug Delivery Systems".
Japanese Published Appli. 7,131,456–Modified PVA Hydrogel Compositions–(1967).

*Primary Examiner*—Douglas W. Robinson
*Attorney, Agent, or Firm*—Barbara L. Renda

[57] ABSTRACT

An ophthalmic gel having an improved intensity and duration of the biological response is provided by utilizing a polyvinyl alcohol-sodium borate gel buffered to a pH of 6.5–8.5.

19 Claims, 1 Drawing Figure

POLYVINYL ALCOHOL OPHTHALMIC GEL

This is a continuation, of application Ser. No. 816,783, filed July 18, 1977 now abandoned.

BACKGROUND OF THE INVENTION

Most ophthalmic medicaments are topically administered to the eye. The most common dosage form for such medicaments is liquid drops. The liquid drop form is easy to apply, but suffers from the inherent disadvantage that the drug it contains is rapidly washed from the precorneal ocular cavity by tear flow. Thus, a continued sustained drug level is not obtained. Sustained levels are typically attained by periodic application of the drops, but this results in frequent administrations by the patient. The result of frequent administration and washing by tear flow is that the level of medication surges to a peak at the time the drops are applied, then the drug concentration falls rapidly.

Other methods of applying ophthalmic medicaments are the unitary ocular inserts. While such inserts deliver the drug in a sustained manner, they suffer from the disadvantages of being difficult to insert and remove, and are expensive.

The prior art discloses a polyvinyl alcohol-boric acid-iodine complex useful in the treatment of eye infections. [*Klin. Oczna.*, 36 (1), 27-32 (1966), C.A. 67:72404r.] However, the researchers concluded that the complex must be maintained at a pH of 5.0-5.5 to afford stability of the iodine. At this pH, the complex is a conventional solution dosage form. Also, this pH is not compatible for use with injured eyes.

OBJECTS OF THE INVENTION

It is an object of our invention to provide a topical ophthalmic medicament which has an improved biological response and an increased duration of activity and a method of use therefor.

It is a further object of our invention to provide a topical ophthalmic medicament which is stable for a prolonged period and gives the medicament for patient use at a pH which is suitable for use even in injured eyes, i.e., a pH of 6.5-8.5.

A further object of our invention is to provide a packaging unit which is delivered to the pharmacist from the manufacturer in a sterile condition, and which thus requires no further sterilization prior to dispensing to the patient.

A still further object of our invention is to provide a patient dosage form which is more convenient and less messy to use than conventional eye drops.

DESCRIPTION OF THE INVENTION

Our invention surprisingly provides a long-acting, topical ophthalmic medicament which has a pH that is compatible with even injured eyes. The present invention relates to a topical ophthalmic gel for use in the eyes of human and domestic animals comprising an ophthalmic medicament in a gel maintained at a pH of 6.5-8.5. More particularly, this invention provides a topical ophthalmic gel comprising:
 0.05-10% by weight of an ophthalmic medicament;
 1-3% by weight of a polyvinyl alcohol;
 0.1-1% by weight of a borate gelling agent; and
 85-99% sterile water; said gel being maintained at a pH of 6.5-8.5.

Ophthalmic drugs suitable for incorporation into the gel of the present invention include, but are not limited to, antibiotics such as tetracycline, chlortetracycline, bacitracin, neomycin, polymixin, gramicidin, oxytetracycline, chloramphenicol, gentamicin, sisomicin, penicillin and erythromycin; antibacterials such as sulfonamides, sulfacetamide, sulfamethizole and sulfisoxazole; antivirals such as idoxuridine and vidarabine; other antibacterial agents such as nitrofurazone and sodium propionate; antiallergenics such as antazoline, methapyriline, chlorpheniramine, pyrilamine and prophenpyridamine; anti-inflammatories such as hydrocortisone, hydrocortisone acetate, dexamethasone, dexamethasone 21-phosphate, fluocinoline, medrysone, prednisolone, methylprednisolone, prednisolone 21-phosphate, prednisolone acetate, fluorometholone, betamethasone, betamethasone valerate, triamcinoline, indomethacin and flunixin; decongestants such as phenylephrine, naphazoline, and tetrahydrozaline; miotics and anticholinesterases such as pilocarpine, eserine salicylate, carbachol, di-isopropyl fluorophosphate, phospholine iodide, and demecarium bromide; mydriatics such as atropine sulfate, cyclopentolate, homatropine, scopolamine, tropicamide, eucatropine and hydroxyamphetamine; and sympathomimetics such as epinephrine.

The ophthalmic drug may be in formulation in its base form, or, optionally in a salt form. Where a salt form is utilized the salt may be any eye-compatible, pharmaceutically acceptable acid addition salt. Such salts can be derived from a variety of organic and inorganic acids such as sulfuric, phosphoric, hydrochloric, hydrobromic, hydriodic, sulfamic, citric, lactic, maleic, malic, succinic, tartaric, cinnamic, acetic, benzoic, gluconic, ascorbic, and nitric. Preferred salts are those utilized in the U.S. Pharmacopeia, XIX edition, given for each individual drug. For instance, atropine is conventionally and preferably formulated as the sulfate, homatropine as the hydrobromide, pilocarpine as the hydrochloride or the nitrate, epinephrine as the bitartrate, physostigmine as the salicylate or sulfate, flunixin as the N-methyl glucamine, gentamicin as the sulfate, and so on.

The polyvinyl alcohol suitable for use in the present invention is typically of the grades of 20 to 100, with a molecular weight of over 10,000, and a viscosity rating of 5-65. A preferred polyvinyl alcohol is of the grade 50 wherein the number 50 indicates the degree of hydrolysis. A second number used in describing suitable polyvinyl alcohols refers to the approximate viscosity in centipoises (measured in 4% aqueous solution at 20° C.). Thus, a polyvinyl alcohol of the grade 50–42 would have a 50% degree of hydrolysis and an approximate viscosity of 42 centipoises measured according to the 9th ed. of the *Merck Index*, 1976.

The gelling agent utilized in this invention to effect formation of the gel may be any of the borate salts such as sodium borate, potassium borate, calcium borate or magnesium borate. Preferably, sodium or potassium borate is used.

Alternatively, the borate may be generated in situ by the reaction of boric acid with aqueous alkali. This is particularly advantageous in the instance where it is desirable to package the components of the gel, i.e., polyvinyl alcohol solution and the borate solution separately. The boric acid may be present in the polyvinyl alcohol solution without effecting formation of the gel. Upon addition of a second solution containing aqueous alkali, the gelling occurs. Suitable aqueous alkali solutions for use in combination with the boric acid include, but are not limited to, sodium hydroxide, potassium hydroxide, sodium carbonate and potassium carbonate. Sodium hydroxide is preferred for use in the invention.

Suitable buffering agents for use in the present invention are those which are typically used in ophthalmic medicinals. Included, but not limited are buffering combinations such as monobasic sodium phosphate - dibasic sodium phosphate ($NaH_2PO_4$—$Na_2HPO_4$), boric acid-sodium borate, and boric acid-sodium acetate. A preferred buffer is the $NaH_2PO_4$—$Na_2HPO_4$ (hereinafter referred to as a phosphate buffer). Most preferably, the amounts of the buffer's components are adjusted so as to afford a final pH of about 7.4 Other salts useful in buffer combinations include sodium and potassium bicarbonate, potassium carbonate and sodium citrate.

Specifically, the amount of buffer can range from about 0.1–5%, preferably about 0.2% for the dibasic component and from about 0.1 to 0.5% for the monobasic component, wherein percentages are by weight based upon the total weight of the overall composition. The ratio of the components is balanced to provide the desired pH for the overall composition.

The gel is usually adjusted in a conventional manner so as to provide an isotonic gel, i.e., a gel wherein the sodium chloride equivalent is about 0.9% by weight of the gel. Preferably, sodium chloride is utilized to adjust the percentage of salt components.

The medicated gel of the present invention may be optionally preserved by the addition of conventional levels of ophthalmic preservatives such as benzalkonium chloride (0.013%), benzethonium chloride (0.01%), phenylmercuric acetate (0.004%), phenylmercuric nitrate (0.004%), chlorobutanol (0.5%), β-phenylethyl alcohol (0.5%) or thiomersal (0.01%).

The ophthalmic medicament is present in the medicated gel in amounts ranging from about 0.05–10% by weight. Particularly suitable amounts for incorporation for the individual drug may be determined by reference to the *U.S. Pharmacopeia*, XIX edition (1970), *Remington's Pharmaceutical Sciences*, 14th edition (1970), or Goodman and Gilman, *The Pharmacological Basis of Therapeutics*, 5th ed., (1976).

Typical preferred gels contain the ophthalmic medicament in the amounts given in Table I below.

TABLE I

| Drug | Preferred Concentration Range (In %) |
| --- | --- |
| Antazoline Phosphate | 0.25–0.5 |
| Atropine Sulfate | 0.5–4.0 |
| Benoxinate Hydrochloride | 0.2–0.4 |
| Betamethasone Phosphate | 0.05–0.5 |
| Carbachol | 0.75–3.0 |
| Cocaine Hydrochloride | 2.0–4.0 |
| Cyclopentolate Hydrochloride | 0.5–2.0 |
| Epinephrine Bitartrate | 1.0–2.0 |
| Fluorescein Sodium | 1.0–2.0 |
| Flunixin NMG (N-methyl glucamine) | 0.5–2.0 |
| Gentamicin Sulfate | 0.1–0.5 |
| Homatropine Hydrobromide | 2.0–5.0 |
| Hydroxyamphetamine Hydrobromide | 0.2–1.0 |
| Idoxuridine | 0.05–0.1 |
| Lidocaine Hydrochloride | 1.0–4.0 |
| Neostigmine Bromide | 1.2–2.5 |
| Phenylephrine Hydrochloride | 0.1–2.5 |
| Physostigmine Salicylate | 0.25–0.5 |
| Physostigmine Sulfate | 0.25–0.5 |
| Pilocarpine Hydrochloride | 0.25–0.5 |
| Pilocarpine Nitrate | 0.5–3.0 |
| Scopolamine Hydrobromide | 0.2–0.5 |
| Tetracaine Hydrochloride | 0.25–0.5 |

TABLE I-continued

| Drug | Preferred Concentration Range (In %) |
| --- | --- |
| Vidarabine | 1.0–3.0 |

Optionally, the gel of the present invention may also contain up to 1% of a conventional eye-compatible stabilizing agent. Suitable stabilizing agents for use in the present invention include, but are not limited to, EDTA, sodium bisulfite, sodium metabisulfite, and thiourea. Most preferably, the stabilizing agent is present in an amount of 0.1–0.2% by weight of the gel.

The gel of the present invention has a shelf life which is dependent upon the particular ophthalmic drug incorporated therein. In the case of drugs which are normally stable in solution of pH 7–9, the usual shelf life of the gel of this invention is at least 1–3 years. For instance, gentamicin sulfate may be formulated into a gel with a shelf life of at least 2 years.

For drugs which are most stable at lower pH's, e.g., 4–7, the shelf life of the gel after formulation is about 3–12 months. For instance, pilocarpine is most stable at a pH of about 4.5 to 5.5. The pH is not suitable for use in the eye since to minimize irritation the pH should preferably be about 6 to 8 and most preferably about 7.4. As noted by *Remington's Pharmaceutical Sciences*, 14th edition, p. 1553, pilocarpine hydrochloride solutions have been shown to need a minimum pH of 6.8 for reasonable eye comfort. However, at a pH of 6.8, the time for 50% decomposition of pilocarpine at 25° C. is 66 days. At elevated temperatures (120° C.) 50% decomposition of pilocarpine in a solution of this pH occurs in about 34 minutes. At a pH of 6.8, pilocarpine is obviously not stable enough for normal shelf life or for autoclaving. Thus, the use of pilocarpine ophthalmic solutions at a pH of 6.8 or above is usually limited to situations where it is possible to constantly prepare fresh solutions of the eye drops for use by the patient by sterile filtration, and have an expiration date of 1 month to take care of the shelf-life problem. Alternatively, a solution having a pH of about 5 is utilized with a long expiration date but which may not be used in cases where the eye has been injured.

To obviate such problems, a gel containing pilocarpine or a salt thereof would be prepared by the dispensing pharmacist just prior to purchase by the patient. Thus, as a preferred embodiment of our invention, the gel is prepared by mixing a sterile solution of the pilocarpine or salt thereof and the polyvinyl alcohol with a sterile, aqueous solution of the borate gelling agent. The pilocarpine/polyvinyl alcohol solution is maintained at a pH of about 4–5 to maintain the stability of the pilocarpine. This pH may be obtained by dissolving the pilocarpine salt in water or, if necessary due to the presence of other excipients, by the addition of a suitable buffer. The borate gelling agent solution contains sufficient buffers to that when the two solutions are mixed to form the gel, the resultant pH will be 6.5–8.5. Depending on the nature of the pilocarpine/polyvinyl alcohol solution, the borate gelling agent solution may or may not require additive buffers to attain this pH.

FIG. 1 illustrates a kit of parts preferred for the packaging of a gel containing an acid stable drug such as pilocarpine or a salt thereof. Containers A and B house the borate gelling agent solution and the drug-polyvinyl alcohol solution, respectively. Caps C and D are closures for the containers A and B. E represents a dispensing-tip and F a sterile closure therefor.

A preferred kit of parts for producing a gel containing an acid stable drug will thus comprise a first container such as labeled as B in FIG. 1 housing an aqueous solution containing the opthalmic medicament and a polyvinyl alcohol, said first solution maintained at a pH to afford stability of the ophthalmic medicament, and a second container such as labeled as A in FIG. 1 housing an aqueous solution containing a gelling agent. The first solution contains the ophthalmic medicament in an amount sufficient to make 0.05–10% by weight when the first solution is mixed with the second solution and the polyvinyl alcohol in an amount sufficient to make 1–3% by weight when the first solution is mixed with the second solution. The second solution contains the borate gelling agent in an amount sufficient to make 0.1–1% by weight when the first solution is mixed with the second solution. The second solution additionally contains buffers in an amount sufficient to afford a pH of 6.5–8.5 when the first solution is mixed with the second solution. If a boric acid and alkali combination is utilized to provide the borate gelling agent, the boric acid is placed in container B and the alkali in container A. Preferably, the two solutions are packaged in a sterile condition with closures such as C and D. Prior to dispensing to the patient, the pharmacist, doctor or nurse, prepares the gel by merely adding the contents of container A to container B. A dispensing tip, such as E shown in FIG. 1, may then be placed on the container B and covered by a sterile closure such as F prior to dispensing to the patient. The patient thus receives a container of the gel which is stable for at least 3 months and which is in an eye-comfortable and convenient dosage form. Most advantageously, the dispensing pharmacist is provided with an eye-compatible system which is in a sterile form when he receives it and thus requires no further sterilization prior to dispensing to the patient.

The gel container will typically be of a suitable size so as to provide an amount of gel sufficient for a multitude of drug applications. The patient is thus provided with a prescription which does not have to be frequently refilled.

The gel itself is well-suited to patient self-administration since its various nature provides a product which does not spill, drip or flow unwantedly from its dispenser. Additionally, and most advantageously, the gel form provides an improved therapeutic effect of enhanced duration. Thus, a patient using a pilocarpine gel will not experience the blurriness of vision towards the end of a treatment period such as is normally experienced by patients using pilocarpine eye drops. This blurriness occurs when the effects of the pilocarpine begin to wear off. Such a side effect is a severe handicap to glaucoma patients using pilocarpine eye drops on a regular and long-term basis since it prevents or restricts normal activities such as reading, sewing and driving. Also advantageously, the enhanced therapeutic effect of the gel dosage form enables the dose of pilocarpine to be lowered, typically to about a 1% pilocarpine gel, while retaining the same degree of biological response. A gel containing 1.0% flunixin NMG likewise provides a suitable anti-inflammatory response while a gel containing 0.2% gentamicin sulfate provides sufficient anti-bacterial effects. Additionally, the gel of this invention is self-dissolving, that is, the tear flow dissolves the gel without leaving a residue.

When preservatives, stabilizers or agents for adjusting the tonicity are used in the gel, and the gel is packaged in two separate compartments, such preservatives or stabilizers may be present in either or both of the solutions. Preferably, however, they are contained in the solution containing the polyvinyl alcohol.

The required daily dosage of the ophthalmic gel will depend on the patient's individual condition and the particular ophthalmic ailment disease state for which the gel is being employed. Typically, 0.05 to 0.8 ml of the gel will be administered 1–3 times per day.

The following examples describe in detail compositions illustrative of the present invention and methods which have been devised for their preparation. It will be apparent to those skilled in the art that many modifications, both of materials and methods, may be practiced without departing from the purpose and intent of this disclosure.

EXAMPLE 1

A pilocarpine gel is prepared by mixing 1 part by volume of a solution consisting of:

| | |
|---|---|
| Pilocarpine hydrochloride | 10.0 mg |
| Polyvinyl alcohol, Grade 50-42 available from Dupont | 40.0 mg |
| Water, sterile USP | q.s. 1.0 ml |
| with 1 part by volume of a solution | |
| consisting of Sodium borate | 7.6 mg |
| Water, sterile USP | q.s. 1.0 ml |

The final gel has a concentration of 0.5% pilocarpine hydrochloride and a pH of 7.0–8.5.

EXAMPLE 2

Substitution of 20.0 mg of pilocarpine hydrochloride for the 10.0 mg of pilocarpine hydrochloride of Example 1 and repetition of the procedure detailed therein affords a medicated gel having a pilocarpine concentration of 1.0% and a pH of 7.0–8.5.

EXAMPLE 3

A pilocarpine hydrochloride gel is prepared by mixing 1 part by volume of a solution consisting of:

| | |
|---|---|
| Pilocarpine hydrochloride | 5.0 mg |
| Polyvinyl alcohol, Grade 99-55 available from Baker | 40.0 mg |
| Water, sterile USP | q.s. 1.0 ml |
| with 1 part by volume of a solution | |
| consisting of Sodium borate | 7.6 mg |
| Water, sterile USP | q.s. 1.0 ml |

The final gel has a concentration of 0.25% pilocarpine hydrochloride and a pH of 7.0–8.5.

EXAMPLE 4

A pilocarpine nitrate gel is prepared by mixing 1 part by volume of a solution consisting of:

| | |
|---|---|
| Pilocarpine nitrate | 10.0 mg |
| Polyvinyl alcohol, Grade 89-6 available from Baker | 30.0 mg |
| Water, sterile USP | q.s. 1.0 ml |
| with 1 part by volume of a solution of | |
| Sodium borate | 7.6 mg |
| Water, sterile USP | q.s. 1.0 ml |

The pilocarpine nitrate concentration of the resulting gel is 0.5% and the pH is 7.0–8.5.

EXAMPLE 5

A pilocarpine hydrochloride gel is prepared by mixing 1 part by volume of a solution consisting of:

| | |
|---|---|
| Pilocarpine hydrochloride | 10.0 mg |
| Polyvinyl alcohol, Grade 50-42 available from Dupont | 40.0 mg |
| Boric acid | 5.0 mg |
| Water, sterile USP | q.s. 1.0 ml |
| with 1 part by volume of a solution of | |
| Sodium hydroxide | 0.4 mg |
| Water, sterile USP | q.s. 1.0 ml |

The pilocarpine hydrochloride concentration of the resulting gel is 0.5% and the pH is 7.0–8.5.

EXAMPLE 6

A pilocarpine hydrochloride gel is prepared by mixing 1 part by volume of a solution consisting of:

| | |
|---|---|
| Pilocarpine hydrochloride | 15.0 mg |
| Polyvinyl alcohol, Grade 50-42 available from Dupont | 20.0 mg |
| Sodium phosphate monobasic | 9.0 mg |
| Sodium phosphate dibasic | 0.1 mg |
| Water, sterile USP | q.s. 1.0 ml |
| with 3 parts by volume of a solution of | |
| Sodium borate | 15.2 ml |
| Water, sterile USP | q.s. 1.0 ml |

This gel has a pilocarpine hydrochloride concentration of 0.375% and a pH of 7.0–8.5.

EXAMPLE 7

A pilocarpine hydrochloride gel is prepared by mixing 1 part by volume of a solution consisting of:

| | |
|---|---|
| Pilocarpine hydrochloride | 10.0 mg |
| Polyvinyl alcohol, Grade 50-42 available from Dupont | 40.0 mg |
| Boric acid | 2.0 mg |
| Water, sterile USP | q.s. 1.0 ml |
| with 1 part by volume of a solution of | |
| Sodium borate | 4.0 mg |
| Water, sterile USP | q.s. 1.0 ml |

This gel has a pilocarpine hydrochloride concentration of 0.5% and a pH of 7.0–8.5.

EXAMPLE 8

A gel is prepared by mixing 1 part by volume of a solution consisting of:

| | |
|---|---|
| Gentamicin sulfate | 4.0 mg |
| Polyvinyl alcohol, Grade 50-42 available from Dupont | 40.0 mg |
| Water, sterile USP | q.s. 1.0 ml |
| with 1 part by volume of a solution consisting of | |
| Sodium borate | 7.6 mg |
| Water, sterile USP | 1.0 ml |

The final gel has a concentration of 0.2% gentamicin sulfate and a pH of 6.5–8.5.

EXAMPLE 9

A gel is prepared by mixing 1 part by volume of a solution consisting of:

| | |
|---|---|
| Flunixin NMG (N-methyl glucamine) | 2.0 mg |
| Polyvinyl alcohol, Grade 50-42 available from Dupont | 40.0 mg |
| Water, sterile USP | q.s. 1.0 ml |
| with 1 part by volume of a solution consisting of Sodium borate | 7.6 mg |
| Water, sterile USP | q.s. 1.0 ml |

The final gel has a concentration of 1.0% flunixin and a pH of 6.5–8.5.

EXAMPLE 10

A gel is prepared by mixing 1 part by volume of a solution consisting of:

| | |
|---|---|
| Betamethasone phosphate | 8.0 mg |
| Polyvinyl alcohol, Grade 50-42 available from Dupont | 40.0 mg |
| Water, sterile USP | q.s. 1.0 ml |
| with 1 part by volume of a solution consisting of | |
| Sodium borate | 7.6 mg |
| Water, sterile USP | q.s. 1.0 ml |

The final gel has a concentration of 0.4% betamethasone phosphate and a pH of 6.5–8.5.

What is claimed is:

1. A topical ophthalmic gel comprising:
   0.05–10% by weight of an ophthalmic medicament;
   1–3% by weight of a polyvinyl alcohol of the grades 20–100, with a molecular weight of over 10,000, and a viscosity rating of 5–65;
   0.1–1% by weight of a borate gelling agent, said borate gelling agent being an alkali metal or alkaline-earth borate salt or being generated in situ by the reaction of boric acid with aqueous alkali; and
   85–99% sterile water; said gel being maintained at a pH of 6.5–8.5.

2. A gel according to claim 1 wherein the ophthalmic medicament is pilocarpine hydrochloride.

3. A gel according to claim 1 wherein the ophthalmic medicament is pilocarpine nitrate.

4. A gel according to claim 1 wherein the ophthalmic medicament is gentamicin sulfate.

5. A gel according to claim 1 wherein the ophthalmic medicament is flunixin N-methyl glucamine.

6. A gel according to claim 1 wherein the ophthalmic medicament is betamethasone phosphate.

7. A gel according to claim 1 wherein the ophthalmic medicament is dexamethasone phosphate.

8. A gel according to claim 1 wherein the borate gelling agent is sodium borate.

9. A gel according to claim 1 wherein the borate gelling agent is generated in situ by boric acid and sodium hydroxide.

10. A gel according to claim 1 wherein the pH is about 7.4.

11. In a method of treating an ophthalmic ailment the improvement which comprises administering topically 0.05 to 0.8 ml of a therapeutic gel according to claim 1, 1–3 times a day.

12. A method according to claim 11 wherein the ophthalmic medicament is pilocarpine hydrochloride.

13. A method according to claim 11 wherein the ophthalmic medicament is pilocarpine nitrate.

14. A method according to claim 11 wherein the ophthalmic medicament is gentamicin sulfate.

15. A method according to claim 11 wherein the ophthalmic medicament is flunixin N-methyl glucamine.

16. A method according to claim 11 wherein the ophthalmic medicament is betamethasone phosphate.

17. A gel according to any of claims 1-7, wherein the ophthalmic medicament is present in an amount of 0.2-0.5 percent by weight.

18. A gel according to claim 17, wherein the pH is 7.0-8.5.

19. A gel according to claim 1, wherein the ophthalmic medicament is gentamicin sulfate and and pH is 7.0-8.5.

* * * * *